US008075928B2

(12) United States Patent
Soma et al.

(10) Patent No.: US 8,075,928 B2
(45) Date of Patent: Dec. 13, 2011

(54) METHOD FOR FERMENTATION AND CULTIVATION, FERMENTED PLANT EXTRACT, FERMENTED PLANT EXTRACT POWDER, AND COMPOSITION CONTAINING THE EXTRACT OF FERMENTED PLANT (75) Inventors: Gen-Ichiro Soma, Tokyo (JP); Chie Kohchi, Hiroshima (JP); Hiroyuki Inagawa, Shimonoseki (JP); Takashi Nishizawa, Tokushima (JP); Yukinori Takahashi, Shimonoseki (JP)

(73) Assignees: Gen-Ichiro Soma, Tokyo (JP); BioMedical Research Group Inc., Tokyo (JP)

( * ) Notice: Subject to any disclaimer, the term of this patent is extended or adjusted under 35 U.S.C. 154(b) by 0 days.

(21) Appl. No.: 10/572,853

(22) PCT Filed: Sep. 22, 2004

(86) PCT No.: PCT/JP2004/013812
§ 371 (c)(1),
(2), (4) Date: Feb. 9, 2007

(87) PCT Pub. No.: WO2005/030938
PCT Pub. Date: Apr. 7, 2005

(65) Prior Publication Data
US 2007/0172492 A1 Jul. 26, 2007

(30) Foreign Application Priority Data

Sep. 26, 2003 (JP) .................................. 2003-336555
May 10, 2004 (JP) .................................. 2004-139761

(51) Int. Cl.
A61K 36/00 (2006.01)
A61K 36/899 (2006.01)
A61K 36/48 (2006.01)
A23L 1/36 (2006.01)
A23L 1/20 (2006.01)
C12N 1/20 (2006.01)

(52) U.S. Cl. ................... 424/750; 424/757; 424/195.17; 424/725; 426/44; 426/46; 435/252.4

(58) Field of Classification Search ........................ None
See application file for complete search history.

(56) References Cited

U.S. PATENT DOCUMENTS

| 5,281,583 | A | | 1/1994 | Soma et al. |
| 5,494,819 | A | * | 2/1996 | Soma et al. ................. 435/252.1 |
| 5,776,756 | A | * | 7/1998 | Kimura et al. ................. 435/189 |
| 2003/0203454 | A1 | * | 10/2003 | Chotani et al. ................. 435/105 |

FOREIGN PATENT DOCUMENTS

| EP | 0 384 798 | | 8/1990 |
| EP | 0 472 467 | A2 | 2/1992 |
| EP | 0 477 050 | | 3/1992 |
| EP | 0 477 050 | A2 | 3/1992 |
| EP | 1 082 908 | | 3/2001 |
| JP | 53-145934 | A | 12/1978 |
| JP | 59-146539 | A | 8/1984 |
| JP | 3-218466 | | 9/1991 |
| JP | 4-49240 | | 2/1992 |
| JP | 4-99481 | | 3/1992 |
| JP | 4-187640 | | 7/1992 |
| JP | 5-155778 | | 6/1993 |
| JP | 05-252937 | A | 10/1993 |
| JP | 6-40937 | | 2/1994 |
| JP | 6-78756 | | 3/1994 |
| JP | 6-90745 | | 4/1994 |
| JP | 8-198902 | | 8/1996 |
| JP | 08-245702 | A | 9/1996 |
| JP | 09-173052 | | 7/1997 |
| WO | WO-99/15690 | | 4/1999 |
| WO | 00/57719 | | 10/2000 |

OTHER PUBLICATIONS

Nagano et al (Characteristics of wheat-flour dough using Enterobacter cloacae GAO with and without yeast, Journal of Food Science 56 (1): 106-108, 1991).*
Inagawa et al, Homeostasis as regulated by activated macrophage. II. LPS of plant origin other than wheat flour and their concomitant bacteria, Chem. Pharm. Bull. 40 (4) 994-997, 1992.*
Mulyowidarso et al, The microbial ecology of soybean soaking for tempe production, International Journal of Food Microbiology, 8 (1989) 35-46.*
Definition of Pantoea agglomerans from Wikipedia, accessed on Mar. 16, 2010, pp. 1.*
Matsuo et al, Suppression of plasma cholesterol elevation by Okara tempe in rats, Biosci Biotech Biochem 57 (7): 1188-1190, 1993.*
Rosell et al, Experimental approach to optimize the use of alpha-amylases in breadmaking, Journal of agricultural and food chemistry 2001, 49 (6): 2973-2977.* Inagawa, H. et al.; "Homeostasis as Regulated by Activated Macrophage. II. LPS of Plant Origin Other than Wheat Flour and Their Concomitant Bacteria;" *Chem. Pharm. Bull.*; vol. 40, No. 4, pp. 994-997 and a cover page. (1992).
Inagawa, H., et al.; "Therapeutic and Protective Effects of a Water Extract of Wheat Flour Having Limulus-Positive Substance (LPSw) Against Several kinds of Diseases;" *Biotherapu*; vol. 5, No. 4, pp. 617-621. (1991).
Soma, G., et al., "Further Developments of the Therapy with Lipopolysaccharides of a Small Molecular Size on Various Intractable Diseases;" *Tumor Necrosis Factor: Molecular and Cellular Biology and Clincal Relevance. Basel, Karger*; pp. 203-220. (1993).
Yamada, T., et al.; "Seibutsugaku Jiten $3^{rd}$ Edition.;" *Iwanami Shoten*; p. 1021 and cover page. (1983).

(Continued)

Primary Examiner — Qiuwen Mi
(74) Attorney, Agent, or Firm — Edwards Wildman Palmer LLP (57) ABSTRACT For the purpose of providing a method of safely and inexpensively producing a fermented plant extract containing an immunopotentiator at a high concentration, the method for fermentation and culture of the present invention ferments a plant component such as wheat flour using *Pantoea agglomerans* which is a gram negative bacterium which lives in a symbiotic relationship with a plant such as wheat and apple. It becomes possible to remarkably augment an immunopotentiation action which the plant has. In addition, these are not contaminated with impurities derived from animal components, and thus these are highly safe.

11 Claims, 1 Drawing Sheet

OTHER PUBLICATIONS

Gavini, F., et al., "Transfer of *Enterobacter agglomerans* (Beijerinck 1888) Ewing and Fife 1972 to *Pantoea* gen. nov. as *Pantoea agglomerans* comb. nov. and Description of Pantoea dispersa sp. nov.;" vol. 39, No. 3, *International Journal of Systematic Bacteriology*; pp. 337-345. (1989).

Nishizawa, T., et al., "Homeostasis as Regulated by Activated Macrophage. I. Lipopolysaccharide (LPS) from Wheat Flour: Isolation, Purification and Some Biological Activities;" *Chem. Pharm. Bull.*; vol. 40, No. 2, pp. 479-483. (1992).

Inagawa, H. et al.; "Homeostasis as Regulated by Activated Macrophage. II. LPS of Plant Origin Other than Wheat Flour and Their Concomitant Bacteria;" *Chem. Pharm. Bull.*; vol. 40, No. 4, pp. 994-997. (1992).

Neilson, A.H.; "Nitrogen Fixation in a Biotype of *Erwinia herbicola* Resembling *Escherichia coli;*" *Journal of Applied Bacteriology*; vol. 46, pp. 483-491. (1979).

Yamada, T., et al.; "Seibutsigaku Jiten $3^{rd}$ Edition.;" *Iwanami Shoten*; pp. 287-288 and cover page. (1983).

Nunes, C., et al.; "Biological control of postharvest pear diseases using a bacterium, *Pantoea agglomerans* CPA-2;" *International Journal of Food Microbiology*; vol. 70, pp. 53-61. (2001).

Nunes, C., et al.; "Post-harvest biological control by *Pantoea agglomerans* (CPA-2) on Golden Delicious apples;" *Journal of Applied Microbiology*; vol. 92, pp. 247-255. (2002).

Asis, C.A. Jr., et al.; "Isolation of endophytic diazotroph *Pantoea agglomerans* and nondiazotroph *Enterobacter asburiae* from sweetpotato stem in Japan;" *Letters in Applied Microbiology*; vol. 38, pp. 19-23. (2003).

Vanneste, J.L., et al.; "Role of Antibiotic Production by *Erwinia herbicola* Eh252 in Biological Control of *Erwinia amylovora;*" *Journal of Bacteriology*; vol. 174, No. 9, pp. 2785-2796. (1992).

Kearns, L.P., et al., "Antibiotic Production by *Erwinia herbicola* Eh1087: Its Role in Inhibition of *Erwinia amylovora* and Partial Characterization of Antibiotic Biosynthesis Genes;" *Applied and Environmental Microbiology*; vol. 64, No. 5, pp. 1837-1844. (1998). (Discussed in the Specification).

Inagawa, H., et al., "Anti-tumor Effect of Lipopolysaccharide by Intradermal Administration as a Novel Drug Delivery System;" *Anticancer Research*; vol. 17, pp. 2153-2158. (1997).

Inagawa, H., et al., "Protective Effect by Intradermal Administration of *Pantea agglomerans* LPS (LPSp) and Oral Administration of ONO-4007;" *Biotherapy*; vol. 11, No. 3, pp. 464-466. (1997).

Nishizawa, T., et al.; "Biological Activities of Lipopolysaccharide Purified from *Pantoea agglomerans;*" *Biotherapy*; vol. 6, No. 3, pp. 356-357. (1992).

Inagawa, H., et al.; "Comparison of Analgesic Effect of Orally Administrated Wheat LPS(LPSw) with Various LPSs from Gram-Negative Bacteria in Mice;" *Biotherapy*; vol. 6, No. 3, pp. 358-359. (1992).

Soma, G.; "Dynamic Aspects of Cytokine Network to induce Anti-tumor Effects by Intradermal Administration of Low Molecular Weight Lipopolysaccharide Derived from *Pantoea agglomerans;*" *Advancement of Pharmaceutical Sciences*; vol. 16, pp. 7-22. (2000).

Hiroko Nagano et al., The Safety of Leavening Bacterium (Enterobacter cloacae GAO) in Wheat Flour Food), Agric. Biol. Chem., 1988, 52(5), p. 1301-1302.

Office Action mailed Oct. 3, 2007, from the Japan Patent Office issued on corresponding Japanese application No. 2007-050166.

Office Action mailed May 30, 2008, issued on the corresponding Chinese patent application.

K.Y. Kim et al., "Enterobacter agglomerans, phosphate solubilizing bacteria, and microbial activity in soil: Effect of carbon sources", Soil Biology and Biochemistry, vol. 30, No. 8-9, Aug. 1998, pp. 995-1003.

H. Inagawa et al., "Homeostasis as Regulated by Activated Macrophage. III. Protective Effect of LPSw (Lipopolysaccharide (LPS) of Wheat Flour) on Gastric Ulcer in Mice as Compared with Those of Other LPS from Various Sources", Chemical and Pharmaceutical Bulletin, vol. 40, No. 4, 1992, pp. 998-1000.

Supplementary European Search Report dated Mar. 25, 2009, issued on the corresponding European patent application No. 04787995.2.

E. Costa et al., "Production of the biocontrol agent *Pantoea agglomerans* strain CPA-2 using commercial products and by-products.", Applied Microbiology and Biotechnology, vol. 56, 2001, p. 367-371.

Examination Report dated Sep. 29, 2009, issued in the corresponding New Zealand Patent Application No. 546551.

Raccach, M. et al., "Natural fermentation of wheat flours," Food Control, vol. 15, No. 3, 2004, pp. 191-195.

Rocha, J. M, et al., "On the Microbiological Profile of Traditional Portuguese Sourdough," Journal of Food Protection, vol. 62, No. 12, 1999, pp. 1416-1429.

Examination Report dated Jul. 15, 2010, issued in the corresponding New Zealand Patent Application No. 546551.

SJ Horn et al., "Production of ethanol from mannitol by *Zymobacter palmae*," Journal of Industrial Microbiology & Biotechnology (2000) 24, 51-57.

Office Action dated Dec. 8, 2010, issued for the corresponding Japanese patent application No. 3008-042509 and English concise explanation of the relevance.

Office Action dated Nov. 17, 2010, issued for the corresponding Taiwanese patent application No. 09920828500 and English concise explanation of the relevance.

Office Action mailed Mar. 9, 2011, issued for the Japanese Patent Application No. 2008-042509 and partial translation thereof.

* cited by examiner

FIG. 1

METHOD FOR FERMENTATION AND CULTIVATION, FERMENTED PLANT EXTRACT, FERMENTED PLANT EXTRACT POWDER, AND COMPOSITION CONTAINING THE EXTRACT OF FERMENTED PLANT

TECHNICAL FIELD

The present invention relates to a method for fermentation and cultivation for obtaining an immunopotentiator which is safe when added in pharmaceuticals, pharmaceuticals for animals, quasi drugs, cosmetics, foods, functional foods, feedstuff, and bath agents for mammals including humans (specifically domestic animals, pet animals, etc.), birds (specifically farmed chicken, pet birds, etc.), amphibian animals, reptiles, fish (specifically aqua cultured fish, pet fish, etc.) and invertebrates, a method for producing a fermented plant extract, a fermented plant extract containing the immunopotentiator obtained by the method for fermentation and culture, powder containing the immunopotentiator obtained from the fermented plant extract and a fermented plant extract composition containing the fermented plant extract.

BACKGROUND ART

It is an urgent problem to establish disease prevention and therapeutic methods including infection prevention technology for the mammals including human (specifically domestic animals, pet animals, etc.), birds (specifically farmed chicken, pet birds, etc.), amphibian animals, reptiles, fish (specifically aqua cultured fish, pet fish, etc.) and invertebrates. Furthermore, in order to achieve this, the methods using no chemicals, without environmental pollution, without producing resistant bacteria and without accumulation in the human body are strongly required. The present inventors have already found for the above problems that the immunopotentiators derived from plants, such as water extract of wheat safely achieve the disease prevention and therapeutic effects (Patent document 1, Non-patent document 1). Also in order to achieve the above object, the present inventors have found that it is possible to use low molecular weight lipopolysaccharides obtained from *Pantoea agglomerans* which is a symbiotic bacterium with wheat (Non-patent document 2). Meanwhile, recent studies have demonstrated that various substances in addition to lipopolysaccharides exhibit the immunopotentiation effect, and these plural natural materials containing the immunopotentiator have attracted attention.

Fermentation technology using bacteria has been commonly used not only in food fields but also broad fields. The fermentation has been widely utilized for the production of alcohols including wines, the production of soy sauces and soybean pastes, the production of fermented milk products such as cheeses, and the production of pharmaceuticals. The bacteria used for these fermentations are many, and rice malt (fungus) yeast and lactic acid bacteria are representative, but it has been rarely reported to use gram-negative bacteria. In general, the fermentation is a phenomenon that organic matter is decomposed by an action of the bacteria, and means in the broad sense that a useful substance is produced by the bacteria (Non-patent document 3). Representatives of the fermentation using the bacteria include wine-making. The wine-making is the fermentation technology using wine yeast adhering to the fruit skin of grapes, and its product is alcohol. In the fermentation technology using the bacteria, as those using gram-negative bacteria, methane fermentation using methane bacteria, acetic fermentation using acetic bacteria and ethanol fermentation (tequila fermentation) from rootstocks of maguey using *Zymomonas mobilis* have been known, but fermentation culture using an edible plant as a material and using the bacteria characterized by living in a symbiotic relationship with the plant have been rarely known, and the immunopotentiator has never attracted attention as a fermented product. Still more, the method for fermentation and culture for the purpose of producing the immunopotentiator has never attracted attention.

Meanwhile, when the fermentation is performed by the bacteria, generally there are nutrient conditions which a fermentation substrate should meet for bacteria growth. That is, the presence of substances available as nutrients by the bacteria is essential, i.e., monosaccharides such as glucose and fructose as carbon sources are sufficiently contained. Therefore, fruits such as grapes containing abundant fructose can be utilized as the fermentation substrate without giving any processing. However, in other cases, a pretreatment such as heating and enzyme treatment for the fermentation by the bacteria is required. For example, the foregoing *Zymomonas mobilis* is a bacterium used for the tequila fermentation. In this case, polysaccharides obtained from the rootstocks of the maguey which is not edible plant are decomposed into fermentable monosaccharides by heating, and subsequently the monosaccharides are fermented by the bacteria to yield the alcohol as the fermentation product. Therefore, when the fermentation culture is performed using a typical bacterium, the polysaccharides such as starch are not suitable as the fermentation substrate. For example, it has been described that *Pantoea agglomerans* cannot decompose starch (Non-patent document 4).

We have demonstrated that an active component for potentiating the immunity is contained in an aqueous extract of wheat flour (Non-patent document 5). We have also demonstrated that the active components are contained in food grains (wheat, rice), seaweeds (brown seaweed, kelp, hijiki (brown alga) and laver) and beans (soybean and adzuki bean) (Non-patent document 6). As this biological activity, it has been found to have preventive effects on human and mouse diseases (diabetes, hyperlipemia, atopic dermatitis, cancer) and can be effective for infection prevention of fish, crustacea and chickens (Patent document 1, Non-patent document 1). However, to expect the above effect by the aqueous extract of wheat flour, it is necessary to ingest the wheat flour in a large amount.

Meanwhile, *Pantoea agglomerans* is a bacterium which lives in a symbiotic relationship with wheat, and is considered to be useful in wheat cultivation because the bacterium supplies phosphorus and nitrogen to the wheat (Non-patent document 7). Also, *Pantoea agglomerans* deposits not only on wheat but also on epidermis of pears and apples. It has been demonstrated in Europe that rot diseases due to fungi can be prevented when this bacterium deposits, and development of utilizing this bacterium as an environmentally friendly fungicide with no toxicity has been advanced (Non-patent document 8). It has been defined that symbiosis is "a phenomenon in which xenogeneic organisms live together. In this case, it is common to mean constantly keeping a behaviorally or physiologically close relationship. Therefore, it does not fall into this concept only to live in the same habitat. Symbiosis is classified and divided into various categories depending on the life meaning and essentiality of the symbiotic partner, sustainability of the relationship and spatial positioning of the symbiotic partner. Generally, the symbiosis is broadly divided into three, mutualism, commensalism and parasitism on the basis of the presence or absence of life benefit/disbenefit of the symbiotic partners." (Non-patent document 9). It has been known that *Pantoea agglomerans* is separated from wheat in any regions and any types (Non-patent document 5) and also separated from fruits (Non-patent documents 10, 11). It has been reported that *Pantoea agglomerans* protects plants from fungi or other bacteria by producing antibiotics (Non-patent documents 12, 13) and performs phosphorus and nitrogen fixation (Non-patent document 7). Therefore, it is considered that *Pantoea agglomerans* is always present in plants and plays a role to give benefits to plants. Thus, its living mode is regarded as "symbiosis" but not "parasitism". In addition, we have demonstrated that the active component to potentiate the immunity is contained in *Pantoea agglomerans*. Also, we have found that the low molecular weight lipopolysaccharide obtained from this bacterium has preventive effects on human and mouse diseases (diabetes, hyperlipemia, atopic dermatitis, cancer) and is effective for infection prevention of fish, crustacea and chickens (Patent document 3, Non-patent document 2).

In such a circumstance, we have conceived the idea of establishing a method for producing a fermented plant extract using *Pantoea agglomerans* as a method for producing a safe and inexpensive immunopotentiator. That is, we have focused on (1) culturing *Pantoea agglomerans* at low cost using a medium containing major protein components included in a culture solution derived from plants as well as fermenting a plant component and (2) preparing materials abundantly containing *Pantoea agglomerans* contained in the plant or a product by fermentation, thereby developing pharmaceuticals, pharmaceuticals for animals, quasi drugs, cosmetics, functional foods, foods, feedstuff and bath agents, for mammals including humans (specifically domestic animals, pet animals, etc.), birds (specifically farmed chicken, pet birds, etc.), amphibian animals, reptiles, fish (specifically aqua cultured fish, pet fish, etc.) and invertebrates. However, this does not mean that the bacteria living in a symbiotic relationship with a plant can directly utilize the plant components, e.g., the material derived from an edible plant as a fermentation substrate. For example, wheat flour is a composite organic substance of starch and the like present in wheat grains, but isolated from *Pantoea agglaomerans* which is a symbiotic bacterium with wheat via the outer skin, and does not directly make contact. Thus, it cannot be demonstrated by a symbiotic relationship of the bacteria with wheat so as to whether *Pantoea agglaomerans* can ferment and be cultured using wheat flour or not. In fact, it has not been known and reported at all that *Pantoea agglaomerans* can assimilate wheat flour. Conversely, on the basis of publicly known facts, it has been described that *Pantoea agglomerans* cannot utilize wheat starch as the fermentation substrate.

Glucides contained in plants are often retained as starch, and this is remarkable in edible plants, particularly food grains. Usually, bacteria do not have a function in which starch is highly assimilated. In this regard, it has been known that a part of facultative gram-negative bacteria can ferment starch. For example, *Erwinia* is known to be able to assimilate starch. However, in this fermentation, when starch is fermented, it is intended to utilize an amylase activity of the bacteria by adding the bacteria cultured in a large amount in another optimal medium, and it has never been conceived that the culture itself is performed using starch and fermentation is performed in conjunction therewith. In the conventional technology, it is regarded as the objective fermentation to only effectively utilize the amylase activity of the bacteria, and it is not scheduled to grow the bacteria using starch as the substrate. Meanwhile, in the Examples of the present invention, it is disclosed that a fermented product is produced in addition to the growth of the bacteria by using starch as an only carbon source, and the present invention is significantly different from the conventional technology in that the present Example is not only fermentation but also fermentation and culture.

On the other hand, if a certain bacterium retains the function to decompose starch, this does not directly mean that the bacteria can grow using starch as the substrate. Upon the culture, in the case of also aiming at the growth of the bacteria, the amount of the bacteria added at the start of the culture is extremely small. In such a case, even if the bacterium lightly has amylase activity, this activity is too weak to sufficiently decompose the substrate and the growth of the bacterium is not achieved. In fact, it has been considered that many of the bacteria cannot grow using starch as the only carbon source.

However, if the fermentation and culture can be performed using *Pantoea Agglomerans* in the medium containing wheat flour as a major component to produce a fermented plant extract (hereinafter, the fermented plant extract obtained by fermentation and culture using *Pantoea Agglomerans* in the medium containing wheat flour as the major component is referred to as a fermented wheat extract) abundantly containing an immunopotentiator at low cost, as specific examples, pharmaceuticals, pharmaceuticals for animals, quasi drugs, cosmetics, foods, functional foods, feedstuff, and bath agents which are environmentally friendly, safe and effective for infection prevention for humans and in the fields of animal industry and aqua culture should be able to be provided. The present invention has been completed by taking the opportunity that it was discovered that *Pantoea Agglomerans* grew using wheat flour as the substrate in the above context and by extensively conducting many experiments.

The fermented plant extract provided by the present invention is a generic term which includes a culture solution itself obtained by performing fermentation and culture, a liquid component obtained by solid/liquid separation of this culture solution, and a liquid component obtained by giving an extraction process to a solid component obtained by the solid/liquid separation, and the like. That is, the fermented plant extract includes the culture solution itself obtained by the method for fermentation and culture according to the present invention, and all extracts capable of being prepared using a whole or a part of the culture solution. Although it is as a matter of course, the fermented plant extract can be utilized by drying as fermented plant extract powder or dissolving the fermented plant extract powder at an optional concentration in an appropriate solution, e.g., phosphate buffer solution including normal saline solution.

[Patent document 1] Japanese Unexamined Patent Application Publication No. H3-218466

[Patent document 2] Japanese Unexamined Patent Application Publication No. H8-198902

[Patent document 3] WO 00/57719

[Patent document 4] Japanese Unexamined Patent Application Publication No. H6-78756

[Patent document 5] Japanese Unexamined Patent Application Publication No. H4-187640

[Patent document 6] Japanese Unexamined Patent Application Publication No. H4-49240

[Patent document 7] Japanese Unexamined Patent Application Publication No. H4-99481

[Patent document 8] Japanese Unexamined Patent Application Publication No. H5-155778

[Non-patent document 1] Inagawa, H. et al., Biotherapy 5(4), p 617-621, 1991

[Non-patent document 2] Soma G. et al., "Tumor necrosis Factor: Molecular and Cellular Biology and Clinical Relevance" p 203-220, 1993

[Non-patent document 3] Yamada T. et al., "Seibutsugaku Jiten" 3rd ed., p 1021, 1983

[Non-patent document 4] Gavini, F. et al., Int. J. Syst. Bacteriol., 39, p 337-345, 1989

[Non-patent document 5] Nishizawa T. et al., Chem. Pharm. Bull., 40(2), p 479-483, 1992

[Non-patent document 6] Inagawa H. et al., Chem. Pharm. Bull., 40(4), p 994-997, 1992

[Non-patent document 7] Neilson A. H., J. Appl. Bacteriol., 46(3), p 483-491, 1979

[Non-patent document 8] Nunes C. et al., Int. J. Food Microbial., 70(1-2), p 53-61, 2001

[Non-patent document 9] Yamada T. et al., "Seibutsugaku Jiten" 3rd ed., p 287-288, 1983

[Non-patent document 10] Nunes C. et al., J. Appl. Microbiol., 92(2), p 247-255, 2002

[Non-patent document 11] Asis C. A. Jr. et al., Lett. Appl. Microbiol., 38(1), p 19-23, 2004

[Non-patent document 12] Vanneste J. L. et al., J. Bacteriol., 174(9), p 2785-2796, 1992

[Non-patent document 13] Kearns L. P. et al., Appl. Environ. Microbial., 64(5), p 1837-1844, 1998

DISCLOSURE OF INVENTION

Problem to be Solved by the Invention

As already described, the immunopotentiators are often contained in plants themselves and are often components or products of the bacteria which live in a symbiotic relationship with the plants. Therefore, to obtain a immunopotentiator derived from natural product which is safe when ingested, it is useful to extract the component from edible plants per se (e.g., limulus positive glycolipid, Patent document 1) or efficiently culture the bacterium which lives in a symbiotic relationship with the edible plant to acquire its component or product (e.g., low molecular weight lipopolysaccharides. Patent document 2). However, immunopotentiator content in the edible plant is extremely small, the food in an extremely large amount must be ingested in order to expect the immunopotentiation effect by eating, and it is generally not easy to keep an ingested amount of the immunopotentiator appropriate. Thus, its effect cannot be expected. Furthermore, when the immunopotentiator is extracted from the plant and utilized as a food or a medicament, high cost is required and it is poor in practicability.

Meanwhile, when focusing on the bacteria which live in a symbiotic relationship with a plant, *Pantoea agglaomerans* which is a symbiotic bacterium with wheat contains a low molecular weight lipopolysaccharide effective for immunostimulation as a component. However, up to now, to extract the low molecular weight lipopolysaccharide, it has been necessary to culture *Pantoea agglaomerans* using an expensive medium in which the major protein contained in the medium is derived from an animal, e.g., NZ amine, trypton or casamino acids. Therefore, it has been difficult to inexpensively provide as a highly common immunopotentiator. Simultaneously, the possibility that unknown harmful substances such as those derived from BSE contaminated animals could not be denied.

In the light of the above problems, the present invention aims at providing a method for fermentation and culture in which an immunopotentiator can be obtained inexpensively and efficiently using safe materials, a fermented plant extract obtained by the method, fermented plant extract powder obtained from the fermented plant extract and a fermented plant extract composition containing the fermented plant extract powder.

Means for Solving the Problem

The method for fermentation and culture of the present invention is characterized in that a material derived from an edible plant and containing a glucides whose major component is a polysaccharide is fermented by a facultative anaerobic gram-negative bacterium which lives in a symbiotic relationship exclusively with a plant and simultaneously the facultative anaerobic gram-negative bacterium is cultured.

The fermentation and culture can be performed in a simple process by fermenting starch as a carbon source by the facultative anaerobic gram-negative bacterium.

It is desirable that the facultative anaerobic gram-negative bacterium is facultative anaerobic bacillus.

It is desirable that the facultative anaerobic bacillus belongs to the family Enterobacteriaceae.

It is desirable that the facultative anaerobic bacillus belongs to the genus *Pantoea, Serratia* or *Enterobacter.*

By making the facultative anaerobic bacillus *Pantoea agglomerans*, it is possible to make starch a carbon source.

It is also desirable that the edible plant is a food grain, seaweed, bean or a mixture thereof.

It is also desirable that the material derived from the food grain is wheat flour, rice powder, wheat bran powder, rice bran or sake lees. In particular, since the wheat flour contains gluten as a protein source, it is possible to efficiently ferment and culture even without using the material derived from an animal.

It is desirable that the material derived from seaweed is brown seaweed powder, "mekabu" (sporophyll of *Undaria pinnatifida*) powder or kelp powder.

When the material derived from bean is bean curd refuse, it contains the protein abundantly. Thus, it is possible to efficiently ferment and culture even without using the material derived from the animal.

The fermented plant extract of the invention is characterized by being obtained by the method for fermentation and culture.

The fermented plant extract powder of the invention is characterized by being obtained from the fermented plant extract.

The fermented plant extract composition of the invention is characterized in that the fermented plant extract or the fermented plant extract powder is combined.

The fermented plant extract compositions may be pharmaceuticals, pharmaceuticals for animals, quasi drugs, cosmetics, foods, functional foods, feedstuff, or bath agents.

It is desirable that the fermented plant extract has the following physicochemical properties.

The fermented plant extract exhibits an ability of macrophage activation even with the presence of polymyxin B. The fermented plant extract has the immunopotentiation effect.

It is desirable that the facultative anaerobic gram-negative bacterium is bacillus belonging to genus *Pantoea* and the edible plant is a food grain, a seaweed or a bean, or a mixture thereof.

It is desirable that the facultative anaerobic gram-negative bacterium is *Pantoea agglomerans* and the edible plant is a food grain, a seaweed or a bean, or a mixture thereof.

It is desirable that the material derived from the food grain is wheat flour, rice powder, wheat bran powder, rice bran or sake lees.

It is desirable that the material derived from the seaweed is brown seaweed powder, mekabu powder or kelp powder.

Effect of the Invention

According to the present invention, since the culture is performed in the medium containing no component derived from an animal, there is no contamination with impurities derived from animal components. Therefore, there is no possibility of unknown harmful substances such as those derived from BSE contaminates, and it is possible to provide a highly safe and inexpensive method for producing fermented plant extract capable of addressing various intended uses and safely and inexpensively provide fermented plant extract or fermented plant extract powder containing the immunopotentiator. Furthermore, it is possible to provide the culture solution, the immunopotentiator and the extract and the extract powder, and further pharmaceuticals, pharmaceuticals for animals, quasi drugs, cosmetics, foods, functional foods, feedstuff, and bath agents containing the extract or the extract powder.

It has never been conceived and there is no fact easily presumed from findings of the conventional fermentation technology that the fermentation and culture can be performed by a simple process that the material derived from an edible plant is exclusively fermented by the facultative anaerobic gram-negative bacterium which lives in a symbiotic relationship with a plant and simultaneously the facultative anaerobic gram-negative bacterium is cultured.

It can be used whether TNF is produced from macrophages or not (TNF induction activity) as an indicator that a certain substance exhibits the immunopotentiation effect. Furthermore, the immunopotentiation effect can be quantified by the amount of produced TNF. Thus, TNF production from the macrophages was examined using a limulus positive plant glycolipid derived from wheat flour and low molecular weight lipopolysaccharide derived from *Pantoea agglaomerans*. The TNF production from the macrophages was stopped by treating with polymyxin B in both the limulus positive plant glycolipid derived from wheat flour and low molecular weight lipopolysaccharide derived from *Pantoea agglaomerans*. However, it was shown in many Examples that even when the fermented plant extract of the present invention was treated with polymyxin B, TNF was produced from the macrophages. This indicates that the fermented plant extract obtained by the fermentation and culture has the immunopotentiation effect qualitatively different from the immunopotentiation effects due to the components of the plant itself which has been the material and the bacteria itself used for the fermentation.

BEST MODE FOR CARRYING OUT THE INVENTION

Suitable embodiments of the present invention will be described in detail below.
I. Essential Feature of Method for Producing Fermented Plant Extract Using *Pantoea agglaomerans*

In the present invention, we have found for the first time that *Pantoea agglaomerans* can grow directly using starch as a carbon source, and have invented a method for inexpensively producing fermented wheat extract abundantly containing the immunopotentiator as a fermented product and a cultured product using *Pantoea agglaomerans*. This can provide environmentally friendly, and safe quasi-drugs, cosmetics, foods, functional foods and feedstuff effective for infection prevention for humans and in the fields of animal industry and aqua culture.
1: Isolation of *Pantoea agglaomerans*

When wheat flour is suspended in water and the supernatant is applied on L broth agar medium and cultured, colonies of bacteria appear. In these colonies, the bacteria are identified by standard methods. For example, those having the same properties as in the standard *Pantoea agglomerans* are selected by selecting the colonies which are gram staining negative, glucose anaerobic metabolism reaction positive and oxidase activity negative and using ID test/EB-20 (Nissui Pharmaceutical Co., Ltd.). The standard *Pantoea agglomerans* is available from the Institute of Physical and Chemical Research, Bioresource Center (Non-patent document 4). In the following description, percentage is a value by weight unless otherwise specified.

2: Evaluation of Immunopotentiation Activity

In the present embodiments, as the indicator of the immunopotentiation effect which the fermented wheat extract exhibits, the ability of macrophage activation was evaluated by TNF production from the macrophages.

3: Low Molecular Weight Lipopolysaccharide Derived from *Pantoea agglomerans*

As one of the active components immunopotentiated by the fermentation and culture using *Pantoea agglaomerans*, it is anticipated to contain low molecular weight lipopolysaccharides derived from *Pantoea agglaomerans*. The low molecular weight lipopolysaccharides have remarkably higher safety and superior biological activity than high molecular weight type lipopolysaccharides (typically lipopolysaccharides) commonly used. Thus, the content of the low molecular weight lipopolysaccharide was measured. Low molecular weight lipopolysaccharides were described in detail in Patent Document 2. The present Example relates to fermented wheat extract, but the present invention does not mean that the plant is limited to wheat and that the immunopotentiator is limited to low molecular weight lipopolysaccharides.

*Pantoea agglomerans* can be cultured using a publicly known method (patent document 2, Non-patent document 8), but major components of proteins contained in the culture medium are derived from the animals, and the medium cost is high. Furthermore, when the functional food and functional feedstuff are given to the animal, or used percutaneously, contamination with impurities derived from the animals typified by BSE is problematic in terms of food safety, and additionally, the production cost becomes high and the method is poor in practicability. Thus, as a result of an extensive study for obtaining a safe and inexpensive natural product having the immunopotentiation action, the present inventors have completed the method for fermentation and culture using *Pantoea agglomerans* for obtaining the fermented wheat extract as shown in the Examples. The major component of the protein contained in the culture medium was conventionally derived from animals, but the present invention made this one derived from plants. Typically, the product obtained by decomposing the protein such as case in derived from cow milk with a digestive enzyme is added to the culture solution. In this case, the prime cost per liter of the medium is about 250 yen, but if this can be replaced with wheat flour, the prime cost becomes about 16 yen. For the purpose of highly concentrating and synergistically fusing the immunopotentiation activity derived from both the plant and the bacteria living in a symbiotic relationship therewith, fermentation has never been performed.

Contents of the invention will be described below as Examples, but the present invention is not limited to *Pantoea agglomerans* as the bacteria, the wheat as an edible plant or wheat flour as the material described in the present Examples. The present invention can also be applied to a material obtained by a typical process from other edible plants containing the immunopotentiator abundantly, e.g., brown seaweed, food grains (containing wheat flour, rice powder, wheat bran powder, rice bran or sake lees which is a material derived from food grains), seaweed (containing brown seaweed powder, mekabu powder or kelp powder which is a material derived from seaweeds), and beans (containing bean curd refuse which is a material derived from beans). It is well-known that proteins and sugars are contained in these plants. These plants can be applied to fermentation and culture using *Pantoea agglaomerans*. It is widely known that indigenous bacteria, e.g., bacteria belonging to the genus *Serratia* or *Enterobacter* live in a symbiotic relationship with these plants (Non-patent document 4). As a matter of course, the bacteria used for the fermentation include facultative anaerobic gram-negative bacteria which live in a symbiotic relationship with these plants.

II: Summary of important points in the present invention (1) The fermented wheat extract itself as the substance having the immunopotentiation action produced by fusion of wheat, *Pantoea agglomerans* which is the symbiotic bacterium therewith and the fermented products by a combination thereof are the subject matter, but the present invention is not limited thereto.

(2) It is new to produce the fermented plant extract using *Pantoea agglaomerans* which is the gram-negative bacterium, but the present invention is not limited thereto.

III: Specific Method for Producing Fermented Wheat Extract (1) *Pantoea agglomerans* is isolated from wheat flour by the standard method (Non-patent document 1). Once being isolated and identified, this bacterium can be stored in 50% glycerol.

(2) 0.05 to 5% salt, 0.005 to 1 mol phosphate buffer, or a mixed salt solution (0.5 to 10% sodium (II) phosphate, 0.05 to 5% potassium (I) phosphate, 0.05 to 5% sodium chloride, 0.05 to 5% ammonium chloride) is prepared.

(3) The wheat flour is suspended at a concentration of 0.05 to 10% in water.

(4) A solution of 0.2 to 3 mol magnesium chloride is prepared.

(5) A solution of 0.2 to 3 mol calcium chloride is prepared.

(6) Solutions of (2) to (5) are sterilized by autoclave, etc., in some cases.

(7) The solutions of (2) to (5) are mixed in appropriate amounts, and water is added to make a suspension containing 0.1 to 5% wheat flour. In some cases, pH is neutralized by adding an alkaline solution or an acidic solution.

(8) In some cases, wheat starch may be partially digested by adding 10 to 50,000 units of amylase per liter of the medium into (7) and incubating at 10 to 80° C. for 1 to 24 hours.

(9) *Pantoea agglomerans* isolated in (1) is added to (7) or (8).

(10) (9) is fermented at 1 to 40° C. In some cases, the fermentation vessel may be left standing or shaken. Alternatively, stirring may be performed every several hours.

(11) (10) is fermented for 6 hours to one week. When the fermentation progresses, the wheat flour solution develops a yellow color.

(12) The alkaline solution may be optionally added during the fermentation of (11) to neutralize the pH, or wheat flour suspension or inorganic salts may be added.

(13) The fermentation is terminated, and a solid component is collected as a precipitate by centrifugation (1,000 to 5,000 rpm, 10 to 60 minutes). The precipitate may be directly used as a fermented wheat flour product for the feedstuff or as the raw material for mixing with the feedstuff.

(14) In the case of producing the fermented wheat extract, (13) is suspended in water or salt buffer, which is then heated at 80 to 140° C. for 10 minutes to 6 hours. The solid component may be removed by centrifuging or filtrating this. The water or the buffer may be added again to the removed precipitate to repeat heating extraction several times.

(15) The fermented wheat extract produced in (14) can be further simply purified depending on intended uses. That is, when the salt such as sodium chloride at a final concentration of 0.05 to 1 mol/L is added to the extract of (14) and subsequently the solvent such as ethanol at one to three times the amount of the extract is added, a precipitate occurs. This may be collected by centrifugation. This precipitate may be further washed with a solvent such as ethanol. When this is dried, powder can be made.

A. Examples Relating to Method for Producing Fermented Wheat Extract

Example 1

Growth Study of *Pantoea agglomerans* in Wheat Flour Medium

In order to confirm whether *Pantoea agglomerans* which is the indigenous symbiotic bacterium with wheat can grow using the wheat flour as the carbon source, the growth of *Pantoea agglomerans* in a wheat flour solid medium was examined.

(1) M9 agar medium containing 0.5% wheat flour as the carbon source was made.

(2) One colony of *Pantoea agglomerans* was picked up from the LB agar medium, and suspended in 1 ml of PBS. This was sequentially diluted 10 times to 10,000 times, and 0.1 ml of each aliquot was seeded on the M9 agar medium of (1).

(3) After culturing at 37° C. for 6 days, appearance of colonies was observed. As a result, about 300 colonies were observed in a petri dish in which 0.1 ml of the dilution 10,000 times had been seeded.

This has confirmed that *Pantoea agglomerans* can utilize wheat flour as the carbon source.

Example 2

Production of Fermented Wheat Extract (1) Distilled water (5 ml) was added to 0.5 g of wheat flour to suspend, 0.1 ml of the supernatant was added to the L broth agar medium, and cultured at 37° C. overnight.

(2) A yellow colony was isolated, a bacterium was identified by the standard methods, *Pantoea agglomerans* was isolated, this was suspended in 50% glycerol solution, and stored in a freezer. A part of this stock was applied on the LB agar medium, which was left standing at 37° C. to make an independent colony of *Pantoea agglaomerans*.

(3) In a 2 liter flask, 64 g of sodium (II) phosphate heptahydrate, 15 g of potassium (I) phosphate, 2.5 g of sodium chloride, and 5 g of ammonium chloride were added and purified water was added to make a total volume one liter (inorganic salt mixed solution). The purified water was added to 13.1 g of magnesium chloride dihydrate to make the total volume 100 ml (magnesium chloride solution). The purified water was added to 11.1 g of calcium chloride to make the total volume 100 ml (calcium chloride solution). The purified water (4 L) was added into a 5 L conical flask (purified water). The above solutions and the purified water were all sterilized by autoclave (TOMY BS-325, 120° C. for 20 minutes).

(4) Wheat flour (24 g) (Nisshin Flour Milling Co., Ltd.) was added to a 1 L conical flask and purified water was added to make the total volume 600 ml. After similarly autoclaving this, 3 mg of α-amylase (SIGMA, Bacillus, enzyme activity of 1500 to 3000 units per mg of the protein) was added, and heated in a water bath at 65° C. for 12 hours (solution of wheat flour treated with amylase).

(5) The prepared solutions and the like in amounts shown in Table 1 were placed in a 3 L sterilized Sakaguchi Flask to make a wheat flour medium.

TABLE 1

| Materials | Dose |
|---|---|
| Inorganic salt mixed solution | 200 ml |
| Purified water | 550 ml |
| Solution of wheat flour treated with amylase | 200 ml |
| Magnesium chloride solution | 2.0 ml |
| Calcium chloride solution | 0.1 ml |

(6) Preparation of inoculum: One colony of *Pantoea agglomerans* isolated from the wheat flour in (2) was added to 10 ml of the wheat flour medium of (5) previously prepared in the same composition, and fermented by gently stirring at 37° C. overnight (12 to 15 hours) to prepare the inoculum for wheat flour fermentation.

(7) The total amount of (6) was added to (5), and fermented at 37° C. for 20 to 30 hours with stirring. pH of the fermented solution was measured and adjusted to pH 7 by adding ammonia water. Sterilely, 150 ml of the solution of wheat flour treated with amylase and 37.5 ml of the inorganic salt mixed solution were added thereto, and similarly fermented for 20 to 30 hours. The same manipulation was repeated to ferment for a total of 65 to 80 hours.

(8) The fermented wheat flour solution was centrifuged (Hitachi, high speed cooling centrifuge, SCR-20B, 5,000 rpm, 20 minutes, 4° C.), and the precipitate was collected.

(9) Phosphate buffer was added to the precipitate of (8), which was then suspended to make the total volume 100 ml, each 33 ml of aliquot was transferred to a 50 ml centrifuge tube, and heat-extracted in a boiling water bath for 30 minutes. After termination of heating, the solution was cooled to room temperature, and centrifuged (Hitachi, high speed cooling centrifuge, SCR-20B, 10,000 rpm, 20 minutes, 20° C.). After the centrifugation, 82 ml of the supernatant with a pale yellow color was collected in another vessel by decantation.

(10) The sodium chloride solution (8.9 ml, 5 mol) was added to 80 ml of the supernatant in (9). When 178 ml of ethanol was added thereto, white turbidity occurred. This was left standing in a freezer (−90° C.) overnight, and then the solution was centrifuged (Hitachi, high speed cooling centrifuge, SCR-20B, 10,000 rpm, 20 minutes, 4° C.). The precipitate was obtained by removing the supernatant. After 10 ml of 70% cooled ethanol was added to the precipitate, which was then suspended, the solution was centrifuged (Hitachi, high speed cooling centrifuge, SCR-20B, 10,000 rpm, 20 minutes, 20° C.), and the precipitate was washed. The precipitate was dried by air and dissolved in distilled water to yield 11 ml of the fermented wheat extract.

(11) Measurement of dried weight: 0.3 ml was transferred to a 1.5 ml plastic tube previously weighed, and after freezing, lyophilization was performed by a lyophilizer, and consequently the weight was 45 mg. Therefore, the dried weight of the fermented wheat extract in (10) was 24.8 mg per 1 ml of the solution and 273 mg per total amount of 11 ml.

(12) The fermented wheat extract was produced 8 times independently by the same method, and the protein amount in each sample was measured by Bradford's method using protein quantification BSA as the standard protein. As comparative subjects, the purified limulus positive glycolipid (Patent document 1) and low molecular lipopolysaccharide (Patent document 2) were used. The measurement results are shown in Table 2. In Tables 2 to 5 and 7, a numerical value for the fermented wheat extract was represented as the content by mg per 1 g of the weight obtained by drying the fermented wheat extract obtained in the above (10).

(13) Measurement of sugar content: The sugar content was measured by a phenol sulfate method using glucose as the standard sugar. The measurement results are shown in Table 3.

(14) Measurement of nucleic acid content: Absorbance at 210 to 340 nm of the sample diluted 100 times was measured. The maximum content was calculated using a value obtained by subtracting the absorbance at 320 nm from the absorbance at 260 nm and 50 kg per 10 D of absorbance as DNA. The measurement results are shown in Table 4.

(15) Measurement of limulus active substance content by limulus assay: For measurement, a Toxi-color system supplied by Seikagaku Corporation was used, and Seikagaku Corporation Et-1 was used as a standard limulus active substance. The measurement results are shown in Table 5.

(16) Iodine-starch reaction: An iodine reagent 1N (10 ml of water was added to 12.7 g of iodine and 25 g of potassium iodide, thoroughly mixed, and then water was added to make 100 ml) was diluted 200 times with water at use. This (5 μL) was added to 0.1 ml of the fermented wheat extract previously dissolved at a concentration of 1 mg/mL, and mixed thoroughly. In the fermented wheat extract, the solution immediately developed a pale purple to dark purple color (positive). In the limulus positive glycolipid and the low molecular weight lipopolysaccharide, the same manipulation did not induce such color development (negative). The above results are summarized in Table 6.

As is evident from the above results, it is obvious that the fermented wheat extract is different from the limulus positive glycolipid and the low molecular weight lipopolysaccharide in protein content, sugar content, nucleic acid content (except the limulus positive glycolipid because of no data), content of the limulus positive substance and iodine-starch reaction. The above results have been simply summarized in Table 7. That is, the fermented plant extract in the present Examples is which is different from the limulus positive glycolipid and the low molecular weight lipopolysaccharide in that it exhibits the following physicochemical properties. The fermented wheat extract exhibits protein content of 5 to 15%, sugar content of 20 to 45%, nucleic acid content of 10 to 35% and limulus positive substance content of 10 to 40%, and is positive in iodine-starch reaction, and exhibits the ability of macrophage activation even with the presence of polymyxin B.

TABLE 2

Protein content in fermented extract

| Sample | Protein content (mg/g) |
| --- | --- |
| Fermented wheat extract 1 | 60 |
| Fermented wheat extract 2 | 71 |
| Fermented wheat extract 3 | 90 |
| Fermented wheat extract 4 | 105 |
| Fermented wheat extract 5 | 103 |
| Fermented wheat extract 6 | 82 |
| Fermented wheat extract 7 | 88 |
| Fermented wheat extract 8 | 88 |
| Limulus positive glycolipid | 40 |
| Low molecular weight lipopolysaccharide | 3.8 or less |

TABLE 3

Sugar content in fermented extract

| Sample | Sugar content (mg/g) |
| --- | --- |
| Fermented wheat extract 1 | 318 |
| Fermented wheat extract 2 | 428 |
| Fermented wheat extract 3 | 313 |
| Fermented wheat extract 4 | 232 |
| Fermented wheat extract 5 | 372 |
| Fermented wheat extract 6 | 324 |
| Fermented wheat extract 7 | 298 |
| Fermented wheat extract 8 | 329 |
| Limulus positive glycolipid | 133 |
| Low molecular weight lipopolysaccharide | 668 |

TABLE 4

Nucleic acid content in fermented extract

| Sample | Nucleic acid content (mg/g) |
| --- | --- |
| Fermented wheat extract 1 | 102 |
| Fermented wheat extract 2 | 102 |
| Fermented wheat extract 3 | 226 |
| Fermented wheat extract 4 | 291 |
| Fermented wheat extract 5 | 302 |
| Fermented wheat extract 6 | 240 |
| Fermented wheat extract 7 | 218 |
| Fermented wheat extract 8 | 216 |
| Limulus positive glycolipid | Unreported |
| Low molecular weight lipopolysaccharide | 2.8 |

TABLE 5

Content of limulus active substance in fermented extract

| Sample | Content of limulus active substance (mg/g) |
| --- | --- |
| Fermented wheat extract 1 | 242 |
| Fermented wheat extract 2 | 118 |
| Fermented wheat extract 3 | 125 |
| Fermented wheat extract 4 | 458 |
| Fermented wheat extract 5 | 224 |
| Fermented wheat extract 6 | 231 |
| Fermented wheat extract 7 | 356 |
| Fermented wheat extract 8 | 289 |
| Limulus positive glycolipid | 970 |
| Low molecular weight lipopolysaccharide | 993 |

TABLE 6

Iodine-starch reaction of fermented extract

| Sample | Determination |
| --- | --- |
| Fermented wheat extract 1 | Positive |
| Fermented wheat extract 2 | Positive |
| Fermented wheat extract 3 | Positive |
| Fermented wheat extract 4 | Positive |
| Fermented wheat extract 5 | Positive |
| Fermented wheat extract 6 | Positive |
| Fermented wheat extract 7 | Positive |
| Fermented wheat extract 8 | Positive |
| Limulus positive glycolipid | Negative |
| Low molecular weight lipopolysaccharide | Negative |

TABLE 7

Summary of differences between fermented wheat extract and similar products

| Sample | Protein content | Sugar content | Nucleic acid content | Content of limulus active substance | Iodine-starch reaction |
| --- | --- | --- | --- | --- | --- |
| Fermented wheat extract (Mean ± Standard deviation) | 86 ± 15 mg/g | 327 ± 57 mg/g | 212 ± 75 mg/g | 255 ± 113 mg/g | Positive |
| Limulus positive glycolipid | Underminus | Underminus | Not measured | Overplus | Negative |
| Low molecular weight lipopolysaccharide | Underminus | Overplus | Underminus | Overplus | Negative |

Underminus: considerably lower values than the range of the values in the fermented wheat extract (mean ± standard deviation)

Overplus: considerably higher values than the range of the values in the fermented wheat extract (mean ± standard deviation)

Example 3

Immunopotentiation Action of Fermented Wheat Extract

An acute myelogenic leukemia cell line, THP-1 ($1\times10^6$/250 µL, RPMI1640 medium containing 10% fetal calf serum) used as human macrophages were placed in a 48-well plate, and previously precultured for 30 minutes. Subsequently, 250 µL of the medium (final volume 500 µL) was added so that the final concentration of each sample was 1 to 10,000 ng/mL. The samples were provided with a group containing polymyxin B (12.5 µg/mL). After culturing for 4 hours, culture supernatants and the cells were collected. The TNF activity in the supernatant was measured by a cytotoxicity test using L-929. The results are shown in Table 8. The macrophages produced TNF even with the presence of polymyxin B by the fermented wheat extract, but with the presence of polymyxin B, the macrophages could not produce TNF by the low molecular weight lipopolysaccharide and the limulus positive glycolipid. From this, it is obvious that the fermented wheat extract has a biological activity different from those of the low molecular weight lipopolysaccharide and the limulus positive glycolipid.

TABLE 8

TNF production from macrophages by fermented wheat extract and inhibitory effect of polymyxin B (TNF induction activity of fermented wheat extract)

| Sample concentration (ng/ml) | Fermented wheat extract with the addition of polymyxin B | Fermented wheat extract without the addition of polymyxin B | Low molecular weight lipopoly-saccharide with the addition of polymyxin B | Low molecular weight lipopoly-saccharide without the addition of polymyxin B | Limulus positive glycolipid with the addition of polymyxin B | Limulus positive glycolipid without the addition of polymyxin B |
|---|---|---|---|---|---|---|
| 0 | 0 | 0 | 0 | 0 | 0 | 0 |
| 1 | 0 | 0 | 0 | 0.64 | 0 | 1.2 |
| 10 | 0 | 1.2 | 0 | 6.3 | 0 | 4.2 |
| 100 | 0 | 8.7 | 0 | 10.2 | 0 | 14.2 |
| 1000 | 1.7 | 28.3 | 0 | 6.3 | 0 | 26.2 |
| 10000 | 26 | 50.4 | 0 | 3.8 | 0 | 13.2 |

B. Application Example of Fermented Wheat Extract to Feedstuff

Example 4

Farmed Chicken Feedstuff Containing Fermented Wheat Extract (Inhibitory Effect of Mortality in Broiler Farming in Large Scale Study)

A feedstuff containing 430 µg/kg of the fermented wheat extract produced in Example 2 was made. Broiler commercial chickens were used with about 5,500 to 6,000 chickens per group. In the control test group, the feedstuff containing no fermented wheat extract was given. The feedstuff containing the fermented wheat extract was given to chickens at 3 weeks of age after hatching, and was administered daily until 7 weeks of age. The number of dead chickens was counted daily. The chickens which did not meet the standard at shipping were discarded. The results are shown in Table 9. A removal rate was 1.9% in the test group (feedstuff containing the fermented wheat extract) which was low, and 3.3% in the control group. A raising rate was 98.1 in the test group and 96.7% in the control group. Thus, a 1.4% increase in the raising rate was observed. A significant difference test in the number of actually shipped chickens and the number of removed chickens between the test group and the control group was conducted, and the significant difference of $p<0.0001$ was observed in $X^2$ test. From the above, the infection protection effect of the feedstuff containing the fermented wheat extract in the broiler farming was shown.

TABLE 9

Effects of feedstuff containing fermented wheat extract on broiler farming

| | Test group | Control group |
|---|---|---|
| Number of chicks | 5906 | 5525 |
| Number of actually shipped chickens | 5792 | 5345 |
| Number of removed chickens | 114 | 180 |
| Removal rate | 1.9% | 3.3% |
| Raising rate | 98.1% | 96.7% |

Example 5

Feedstuff for Cultured Fish Containing Fermented Wheat Extract (Infection Prevention Effect in Yellowtail Open Air Test)

For examining the infection prevention effect, about 5,200 yellowtails per group in an open air test were raised by the feedstuff containing the fermented wheat extract produced in Example 2. The results are shown in Table 10. The mortality due to *Streptococcus* in a non-administration control group reached 4.8%. In the group in which 100 µg/kg/day (per body weight 1 kg and per one day) was ingested (test group), the mortality was observed to be significantly reduced ($p<0.00001$) compared with the non-administration group (control group).

TABLE 10

Infection prevention effect of feedstuff containing fermented wheat extract on yellowtails in open-air test

| Treatment | Number of fish raised | Number of fish died | Mortality | Significant difference test ($X^2$ test) |
|---|---|---|---|---|
| Control group | 5201 | 249 | 4.79 | |
| Test group | 5193 | 101 | 1.94 | (P < 0.00001) |

Example 6

Feedstuff for Cultured Fish Containing Fermented Wheat Extract (Infection Prevention Effect on Koi Herpes)

(1) Carp: Black carp whose body weight was 70 g were used. The test was conducted using 20 carp per group.

(2) Preparation of koi herpes virus: 10 ml of Hanks balanced salt solution (HBSS) buffer was added to 1 g of branchi of the carp that died from infection by koi herpes, and homogenated, filtrated with a filer of 0.45 μm, and its filtrate was made a virus solution.

(3) Infection with koi herpes virus: The above filtrate (600 μL/100 g body weight) was injected intraperitoneally.

(4) Preparation of feedstuff containing fermented wheat extract: 0, 5, 10 and 20 mg/kg of the fermented wheat extracts produced in Example 2 were mixed with the commercially available feedstuff.

(5) Feeding method: Each feedstuff of 1% weight per body weight was given once a day. This corresponds to 0, 50, 100 or 200 μg/kg body weight/day in terms of the mount of the fermented wheat extract.

Figure 1:
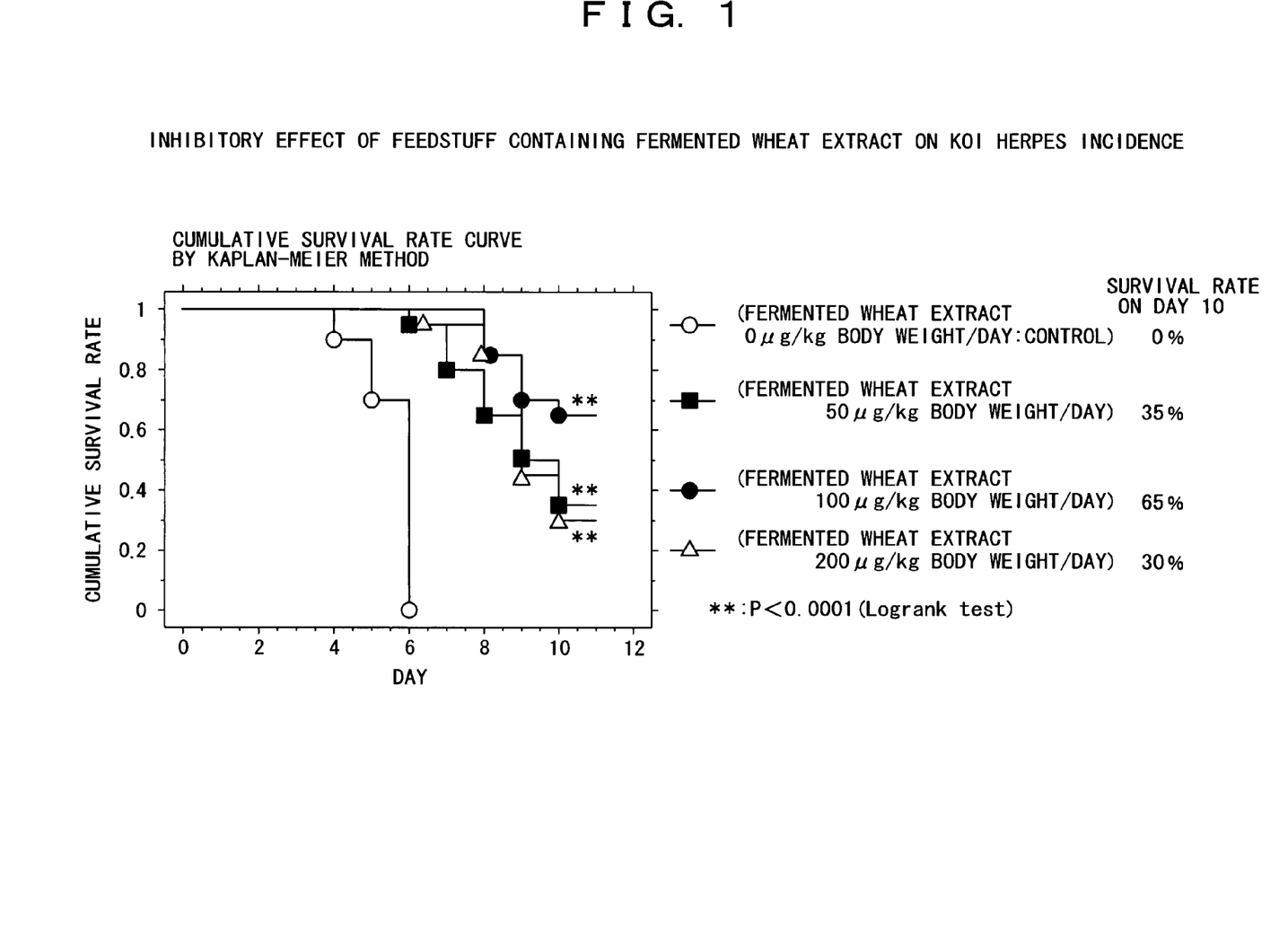
FIG. 1 is a view showing inhibitory effects of koi herpes occurrence by feedstuff containing a fermented wheat extract.

(6) Experiment: The feedstuff containing the fermented wheat extract was given for a week, then the carp were infected with the virus, and subsequently the feedstuff containing the fermented wheat extract was given for 10 days. A survival rate of the carp for 10 days after the infection with the virus was observed. The results are shown in FIG. 1.

All carp by the end of the sixth day died in the group in which the fermented wheat extract had not been given. Meanwhile, it was shown that in the groups in which the fermented wheat extract had been given, the survival rate was significantly increased on day 10 after infection (Kaplan Meier method, log rank test, percentage of risk was 0.01% or less). In particular, the survival rate of 65% was shown in the group in which 100 μg/kg body weight/day of the fermented wheat extract was given.

C. Application Examples of Fermented Wheat Extract to Cosmetics and Bath Agents

Example 7

Production of Hand Cream Containing Fermented Wheat Extract

The fermented wheat extract at around 10% produced in Example 2 was mixed with an ointment of a fat-soluble substrate 1 in a formulation described in table 11 to obtain the ointment.

TABLE 11

| Composition | Dose |
|---|---|
| White petrolatum | 250 g |
| Stearyl alcohol | 200 g |
| Propylene alcohol | 120 g |
| Polyoxyethylene cured castor oil 60 | 40 g |
| Glycerine monostearate | 10 g |
| Methyl paraoxybenzoate | 1 g |
| Propyl paraoxybenzoate | 1 g |
| Purified water | Reasonable quantity |

Example 8

Production of Moisturizing Cream Containing Fermented Wheat Extract

1. Formulation of Moisturizing Cream Containing Fermented Wheat Extract

Components used are shown in Table 12. The combination A was heated and dissolved at 70° C., the combination B mixed in purified water in a ¼ amount and heated/dissolved at 70° C. and the combination C mixed in purified water in a ¼ amount and heated/dissolved at 70° C. were added thereto. The mixture was thoroughly mixed by a homogenizer and then cooled to 40° C. The combination D was then added thereto, and pH was adjusted to 6.8. Subsequently, remaining purified water and fermented wheat extract produced in Example 2 in an appropriate amount were added there to, and thoroughly mixed to obtain a milky lotion. The fermented wheat extract was previously dissolved at 5 mg/mL in purified water, and 0.1 ml thereof was added to 100 g of the milky lotion.

TABLE 12

| Components | w/w % | Combination |
|---|---|---|
| Squalane | 5.0 | A |
| Olive oil | 10.0 | A |
| Jojoba oil | 5.0 | A |
| Stearic acid | 4.0 | A |
| Polyoxyethylene sorbitan monostearate (20 E.O.) | 1.8 | A |
| Methyl polysiloxane | 0.3 | A |
| Sorbitan monostearate | 0.5 | B |
| Self-emulsified type glycerine monostearate | 3.0 | B |
| Propyl paraoxybenzoate | 0.2 | B |
| Methyl paraoxybenzoate | 0.2 | B |
| 1,3-Butylene glycol | 5.0 | B |
| Concentrated glycerine | 6.0 | B |
| Carboxy vinyl polymer | 0.22 | C |
| Potassium hydoxide | Reasonable quantity | D |
| Fermented wheat extract (5 mg/ml) | 0.1 | |
| Purified water | Reasonable quantity | |
| Total amount | 100.00 | |

2. Effect of Moisturizing Cream Containing Fermented Wheat Extract

This cream was used by 43 men and women, and a questionnaire survey was conducted. As a result, for the moisturizing effect, 18 people answered that there was certainly a moisturizing effect, 18 people answered that there was a slight moisturizing effect, 2 people answered that there was no moisturizing effect, and 5 people did not answer (one specimen sign test: p<0.0001). For an improvement effect on rough skin, 6 people answered that it had been certainly effective, 13 people answered that it had been slightly effective, no people answered that there had been no effect, and 24 people did not answer (one specimen sign test: p<0.0001). For deterioration of skin condition after use, no people answered that there had been deterioration. This cream was used by 4 people with mild atopic symptoms, and the questionnaire survey was conducted. For the improvement of atopic dermatitis, 3 people answered that it had been certainly effective, and one answered that it had been slightly effective (one specimen sign test: p<0.125). Additionally, one answered that acne scars had rapidly recovered. This cream was used by 9 men after shaving, and the questionnaire survey was conducted. Eight men answered that it had been effective for a reduction of pain after shaving, prevention of dryness and early healing of razor cuts (one specimen sign test: p<0.01). In addition, this cream was used by 2 people having the symptoms of stiff shoulders due to age by applying on the shoulder to reduce the pain. One answered that it had been effective.

In addition, this cream was used for patients with burn injuries. In patients having burn injuries on the skin of both hands to the same extent, the cream containing the fermented wheat extract produced in Example 2 was applied on one hand, and the cream containing no fermented wheat extract was applied on the other hand. The hand treated with the cream containing the fermented wheat extract obviously recovered faster. This cream was used for 10 patients with burn injuries including this case. Consequently, in all sites treated with the cream containing the fermented wheat extract, wounds recovered faster than in the sites treated with the cream containing no fermented wheat extract (Fisher's exact probability: $p<0.001$). From the above, it was shown that the fermented wheat extract exhibited the therapeutic effect on the burn injuries.

Example 9

Production of Skin Lotion Containing Fermented Wheat Extract

1. Formulation of Skin Lotion Containing Fermented Wheat Extract

Components used are shown in Table 13. The fermented wheat extract produced in Example 2 was previously dissolved at 5 mg/mL in purified water, and 0.1 ml thereof was added to 100 g of the skin lotion.

TABLE 13

| Components | % |
| --- | --- |
| Sodium citrate | 0.1 |
| Pyrrolidone sodium carboxylate | 1.0 |
| 1,3-Butylene glycol | 5.0 |
| POE(30) POP(6) Decyltetradecyl ether | 0.6 |
| Purified water | Reasonable quantity |
| Fermented wheat extract (5 mg/ml) | 0.1 |
| Preservative | Reasonable quantity |
| Ethanol | 10.0 |
| Total amount | 100.0 |

2. Effects of Skin Lotion Containing Fermented Wheat Extract

This skin lotion was used by 5 women, and the questionnaire survey was conducted. As a result, 3 women answered that it had the good moisturizing action, and 2 women answered that it had the usual moisturizing action. Non of the women had skin trouble.

Example 10

Production of Bath Agent Containing Fermented Wheat Extract

A bath agent containing the fermented wheat extract was made for the purpose of improving body functions. Basic components of the bath agent are shown in Table 14.

TABLE 14

| Components | Content |
| --- | --- |
| Sodium sulfate | 25.0 g |
| Calcium silicate | 0.26 g |
| Perfume (yuzu (*citrus junos*)) | 0.5 g |

The bath agent containing the fermented wheat extract was made by adding 110 μg of the fermented wheat extract produced in Example 2 to the above components. The bath agent contained the extract and the bath agent containing no extract were blindly given to 102 subjects, who then used them in a bathtub (160 to 200 liters) upon taking a bath, and the questionnaires [(1) warming degree of a body, (2) difficulty of feeling cold after bath, (3) fatigue recovery effect, (4) easiness in falling asleep, (5) recovery degree of stiffness in the shoulder, (6) effect on muscle pain, (7) effect on nerve pain, (8) effect on lower back pain, (9) effect on sensitivity to cold temperatures, (10) improvement effect on foot ringworm, (11) improvement effect on dry skin, (12) effect on atopic dermatitis] were conducted. As a result, 7% or more improvement compared with the control was observed in (1) the warming degree of a body (10%), (2) the difficulty of feeling cold after the bath (7.9%), (6) the effect on muscle pain (13%), (8) the effect on lower back pain (16%), (9) the effect on sensitivity to cold temperatures (10%) and (11) the improvement effect on dry skin (7.3%) (Mantel-Haenszel test: $p<0.04$). From the above results, relaxation effects on pains and improvement in the warming of the body were observed by using the fermented wheat extract as the bath agent.

D. Application Example of Fermented Wheat Extract to Functional Foods

Example 11

Production of Candy Containing Fermented Wheat Extract (1) As raw materials, granulated sugar, starch syrup, mixture of water and the fermented wheat extract produced in Example 2 were mixed at a ratio of 5:5:5:1, and cooked down by heating at 120 to 160° C.

(2) The candies were obtained by cooling one obtained in (1) on a steel plate for cooling, extending in a stick shape, and molding into grain shapes of around 1 g.

The present candies in an appropriate amount were placed in 20 ml of water, and dissolved by heating. The amount of lipopolysaccharide as the fermented wheat extract active component was measured in this solution, and consequently it was 4.6 μg/g. This candy was ingested by 6 men and women who had caught a cold and had a sore throat. Thereafter, the questionnaire survey for the sore throat was conducted. For the sore throat, all 6 people felt a reduced sore throat (one specimen sign test: $p<0.03$).

Example 12

Production of Alcohol Decomposition Functional Food Containing Fermented Wheat Extract The fermented wheat extract produced in Example 2 was mixed with a commercially available product as an alcohol decomposition functional food, and it was examined whether alleviation of pharyngodynia as a new action was observed or not.

Commercially available product: trademark "Nonde oiki"
The components are shown in Table 15.

TABLE 15

| Components | Component content rate |
| --- | --- |
| Powder sugar | 78.98% |
| Vitamin C | 10.00% |
| Toyoriden-P | 5.00% |
| Vitamin B2 | 0.02% |
| Perfume (menthol) | 0.50% |
| Amachazuru (*Gynostemma pentaphylla*) (saponin) | 3.50% |
| T-Flavor Conc 13189B (flavonoid) | 2.00% |

Current "Nonde oiki" contains the extract of amachazuru (*Gynostemma pentaphylla*) and the extract of green tea, but contains only about 0.002 μg per pack of lipopolysaccharide which is one of the active components of the plant extract. Therefore, it is anticipated to acquire a new function by adding the appropriate amount of fermented wheat extract which abundantly contains lipopolysaccharide. It is desirable to combine 1 to 30 μg per 2 g pack of lipopolysaccharide which is one of the active components of the fermented wheat extract (5 to 150 μg as the fermented wheat extract). Thus, first, the product in which 50 μg of the fermented wheat extract had been combined in one pack was produced. In the production process of Nonde oiki, 2.5 mg of the fermented wheat extract was added per 100 g of the product. As a result, a new product which contained 50 μg of the fermented wheat extract per 2 g product was produced.

Subjecting 20 adult men and women who complained of pharyngodynia after drinking and enjoying karaoke, conventional "Nonde oiki" and "Nonde oiki" containing the fermented wheat extract were given to 10 people, respectively, and an enhanced action of an alcohol decomposition ability which was the publicly known action and an alleviation effect on the pharyngodynia were examined. Immediately thereafter, the questionnaire survey for the alleviation effect on the pharyngodynia was conducted. As a result, reduction of the pharyngodynia was observed in 8 of 10 people who had received "Nonde oiki" containing the fermented wheat extract" but 2 of 10 people who had received conventional "Nonde oiki." Thus, a statistically significant difference (Fisher's exact probability: p<0.012) was observed compared with the control.

E. Example Relating of Medicinal Benefits of Fermented Wheat Extract

Example 13

Production of Glycerol Solution Containing Fermented Wheat Extract (Therapeutic Effect on Atopic Dermatitis)

A 50% glycerol solution containing 50 μg/mL of the fermented wheat extract produced in Example 2 was given 2 or 3 times daily with a dosage of 2 to 3 ml per administration to 9 male and female patients with refractory atopic dermatitis (25 to 34 of age) where rashes were observed on the face, hands and legs, main body, neck, arms and back and subjective symptoms were moderate to severe. The subjective symptoms (pruritus) were classified into mild, moderate and severe levels by patients complains. Two weeks to two months after the start of use, the patients visited again, and the effects were evaluated. In the results, the cases of complete response (remarkable improvement of rashes and almost disappearance of the subjective symptom) was 4 (44%), the cases of partial response (slight improvement of rashes and reduction in the subjective symptom) was 4 (44%), the case of no change was one (11%) and the case of deterioration was 0 (one specimen sign test: p<0.03). From the above result, an effective rate was determined to be 89%.

Example 14

Analgesic Effect of Fermented Wheat Extract

The fermented wheat extract produced in Example 2 was dissolved in distilled water, and 0.2 ml thereof per mouse was orally administered to mice using a sonde. After 90 minutes, 0.7% acetic acid was intraperitoneally administered to the mice. After observing the mice for 5 minutes, the number of wriggles caused for 30 minutes was counted. The results are shown in Table 16 as the amount of each sample required for inhibiting 30% of the wriggle number in the control of distilled water. When the effective activity of the low molecular weight lipopolysaccharide derived from *Escherichia coli* was 1, the effective activity of the fermented wheat extract was 7, showing that the fermented wheat extract exhibited an excellent analgesic effect.

TABLE 16

Analgesic effect of fermented wheat extract on pain induced by acetic acid in mice

| Treatment | Amount for inducing 30% inhibition | Relative activity |
|---|---|---|
| Distilled water | 230 ± 190 mg | 1 |
| Fermented wheat extract | 33 ± 35 mg | 7.0 |

Example 15

Inhibitory Effect of Fermented Wheat Extract on Atopic Dermatitis

In order to examine the effect of the fermented wheat extract on atopic dermatitis, an I type allergy model was introduced. Anti-dinitrophenyl monoclonal antibody (1 μg/mouse) was intravenously administered to male BALB/c mice (3 to 4 per group). After one hour, the fermented wheat extract produced in Example 2 was administered intracutaneously (abdominal site) (4 μg/mouse) or orally (100 μg/mouse). After an additional one hour, 20 μL of acetone-olive oil mixed (4:1) solution containing 0.25% dinitrofluorobenzene was applied as an allergen on the surface and backface of an ear pinna of a mouse. A thickness of the ear pinna was measured using a thickness gauge 1, 2, 24 and 48 hours after application. The value (Δ) obtained by subtracting the thickness just before application was a level of edema. The effect of drug administration was evaluated by the inhibitory rate obtained by the following formula in the inhibition in an early phase reaction observed one hour after the allergen administration and a delayed reaction induced after 24 hours. Inhibitory rate=(1−ΔEdema of ear pinna after drug administration/ΔEdema of ear pinna in control×100. The results are shown in Table 17. As is evident from the table, the fermented wheat extract inhibited an allergic reaction by both intracutaneous and oral administrations.

TABLE 17

Inhibitory effect of fermented wheat extract on allergic reaction

| Administration method of fermented wheat extract | Dosage (/mouse) | Inhibitory rate (%) (after one hour) | Inhibitory rate (%) (after 24 hour) |
|---|---|---|---|
| Intracutaneous administration | 4 μg | 81.0 | 102.1 |
| Oral administration | 100 μg | 41.3 | 60.8 |

Example 16

Infection Prevention Effect of Fermented Wheat Extract

In order to examine the infection prevention effect of the fermented wheat extract, methicillin-resistant *Staphylococcus aureus* (MRSA) infection model was introduced. Cyclophosphamide (CY, 200 mg/kg) was intraperitoneally administered to male BALB/c mice (6 to 8 weeks of age) (10 per group), and after 5 days, the fermented wheat extract produced in Example 2 was administered intracutaneously. After 3 hours, MRSA ($3\times10^7$ colony forming units (CFU)) was administered intravenously, and the number of survival days was examined. The results are shown in Table 18. As is evident from the table, the fermented wheat extract exhibited the infection prevention effect on MRSA with a statistically significant difference ($X^2$ test: $p<0.001$) compared with the saline group (control).

TABLE 18

Prevention effect of fermented wheat extract on MRSA infection

| Administered medicament | Survival rate | Risk rate |
|---|---|---|
| Saline | 0/10 | |
| Fermented wheat extract (0.004 μg) | 9/10 | P < 0.001 |
| Fermented wheat extract (0.04 μg) | 6/10 | P < 0.005 |

Example 17

Therapeutic Effect of Fermented Wheat Extract on Metastatic Cancer

In order to examine the therapeutic effect of the fermented wheat extract on metastatic cancer, a lung metastasis model of Meth A cells was introduced. The Meth A cancer cells ($1\times10^5$ cells) were intravenously administered to male BALB/c mice (6 to 8 weeks of age) (10 per group), and after 12 days, the fermented wheat extract produced in Example 2 was administered intracutaneously for 4 consecutive days. Twenty days after transplanting the cells, an autopsy was performed, the lung was extracted and fixed with formalin. The lung was observed by the naked eye and the number of nodes was counted. The results are shown in Table 19. As is evident from the table, the fermented wheat extract exhibited the therapeutic effect on meth A lung metastatic cancer with a statistically significant difference (t-test: $p<0.001$) compared with the saline group (control).

TABLE 19

Therapeutic effect of fermented wheat extract on Meth A lung metastatic cancer

| Administered medicament | Number of nodes (Mean ± Standard deviation) | Risk rate |
|---|---|---|
| Saline | 60 ± 11 | |
| Fermented wheat extract (40 μg/kg) | 33 ± 8 | P < 0.001 |
| Fermented wheat extract (400 μg/kg) | 19 ± 6 | P < 0.001 |

F. Examples Relating to Fermented Bean Curd Refuse Extract

Example 18

Production of Fermented Bean Curd Refuse Extract (1) 1.0 L of water, 0.2 g of potassium (I) phosphate, 1.15 g of sodium II phosphate, 8 g of common salt and 0.2 g of potassium chloride were added to a 2 liter conical flask.

(2) A dried bean curd refuse (20 g) was added to (1).

(3) (2) was sterilized by autoclave.

(4) Preparation of inoculum: One colony of *Pantoea agglomerans* isolated from wheat flour was added to 5 ml of 2% bean curd refuse medium previously prepared in the same composition, and fermented at 37° C. overnight (15 hours) by gently stirring to prepare the inoculum for fermentation of the bean curd refuse.

(5) The total amount of (4) was added to (3), and fermented at 37° C. for 48 hours by gently stirring.

(6) The fermented bean curd refuse solution of (5) was extracted by heating at 120° C. for 20 minutes in the autoclave. This was centrifuged (Kubota 8800, 2,000 rpm, 10 minutes), and the supernatant was collected to make a fermented bean curd refuse extract.

(7) Measurement of dried weight: 0.3 ml was transferred to a 1.5 ml plastic tube previously weighed, and after freezing, lyophilization was performed by the lyophilizer, and consequently the weight was 5.97 mg. Therefore, the dried weight of the fermented bean curd refuse extract of (6) was 19.9 mg per 1 ml of the solution and 19.9 g per total amount of 1,000 ml.

(8) The protein amount was measured in the sample diluted 10 times by Bradford's method using protein quantification BSA as the standard protein. The results are shown in Table 15.

(9) Measurement of nucleic acid content: Absorbance at 210 to 340 nm of the sample diluted 100 times was measured. The maximum content was calculated using a value obtained by subtracting the absorbance at 320 nm from the absorbance at 260 nm and 50 μg per 1 OD of absorbance as DNA.

(10) Measurement of sugar content: The sugar content was measured by the phenol sulfate method using glucose as the standard sugar.

(11) Measurement of limulus active substance content by limulus assay: For measurement, a Toxi-color system supplied by Seikagaku Corporation was used, and Seikagaku Corporation Et-1 was used as the standard limulus active substance. The results are shown in Table 20.

TABLE 20

Component contents in fermented bean curd refuse extract

| Components | (mg/g) |
|---|---|
| Protein | 112 |
| Sugar | 537 |
| Nucleic acid | Undetectable |
| Limulus active substance | 10 |

Example 19

Immunopotentiation Action of Fermented Bean Curd Refuse Extract

An acute myelogenic leukemia cell line, THP-1 ($1\times10^6$/250 μL, RPMI1640 medium containing 10% fetal calf serum) used as human macrophages were placed in a 48-well plate, and previously precultured for 30 minutes. Subsequently, 250 μL of the medium (final volume 500 μL) was added so that the final concentration of each sample was 100 to 10,000 ng/mL. The samples were provided with a group containing polymyxin B (12.5 μg/mL) (no group containing polymyxin B only at 100 ng/mL). After culturing for 4 hours, culture supernatants and the cells were collected. The TNF activity in the supernatant was measured by a cytotoxicity test using L-929. The results are shown in Table 21. The macrophages produced TNF even with the presence of polymyxin B by the fermented bean curd refuse extract, but with the presence of polymyxin B, the macrophages could not produce TNF by the low molecular weight lipopolysaccharide. From this, it is obvious that the fermented bean curd refuse extract has a biological activity different from those of the low molecular weight lipopolysaccharide.

myxin B (12.5 μg/mL). After culturing for 4 hours, culture supernatants and the cells were collected. The TNF activity in the supernatants was measured by a cytotoxicity test using L-929. The results are shown in Table 22. The macrophages produced TNF even with the presence of polymyxin B by the fermented rice powder extract, but with the presence of poly-

TABLE 21

TNF production from macrophages by fermented bean curd refuse extract and inhibitory effect of polymyxin B (TNF induction activity of fermented bean curd refuse extract)
TNF induction activity of fermented bean curd refuse extract and inhibitory effect of polymyxin B (TNF activity)

| Sample concentration (ng/ml) | Fermented bean curd refuse extract with the addition of polymyxin B | Fermented bean curd refuse extract without the addition of polymyxin B | Low molecular weight lipopoly-saccharide with the addition of polymyxin B | Low molecular weight lipopoly-saccharide without the addition of polymyxin B | Limulus positive glycolipid with the addition of polymyxin B | Limulus positive glycolipid without the addition of polymyxin B |
|---|---|---|---|---|---|---|
| 0 | 0 | 0 | 0 | 0 | 0 | 0 |
| 100 | N.D. | 0.45 | 0 | 0.39 | 0 | 3.27 |
| 1000 | 0.38 | 4.6 | 0 | 0.42 | 0.5 | 11.3 |
| 10000 | 11.1 | 11.1 | 0 | 0.28 | 14.4 | 25.3 |

N.D.: Not done

G. Examples Relating to Fermented Rice Powder Extract

Example 20

Production of Fermented Rice Powder Extract (1) 1.0 L of water, 0.2 g of potassium (I) phosphate, 1.15 g of sodium II phosphate, 8 g of common salt and 0.2 g of potassium chloride were added to a 2 liter conical flask.

(2) A dried rice powder (20 g) was added to (1).

(3) (2) was sterilized by autoclave.

(4) Preparation of inoculum: One colony of *Pantoea agglomerans* isolated from wheat flour was added to 5 ml of a 2% rice powder medium previously prepared in the same composition, and fermented at 37° C. overnight (15 hours) by gently stirring to prepare the inoculum for the fermentation of the rice powder.

(5) The total amount of (4) was added to (3), and fermented at 37° C. for 72 hours by gently stirring.

(6) The fermented rice powder solution of (5) was extracted by heating at 120° C. for 20 minutes in the autoclave. This was centrifuged (Kubota 8800, 2,000 rpm, 10 minutes), and the supernatant was collected to make a fermented rice powder extract.

(7) Measurement of limulus active substance content by limulus assay: For measurement, Toxi-color system supplied by Seikagaku Corporation was used, and Seikagaku Corporation Et-1 was used as the standard limulus active substance. The content of the limulus active substance in the fermented rice powder extract was measured to be 1.7 μg/mL.

Example 21

Immunopotentiation Action of Fermented Rice Powder Extract

An acute myelogenic leukemia cell line, THP-1 ($1\times10^6$/250 μL, RPMI1640 medium containing 10% fetal calf serum) used as human macrophages were placed in a 48-well plate, and previously precultured for 30 minutes. Subsequently, 250 μL of the medium (final volume 500 μL) was added so that the final concentration of each sample was 1 to 10,000 ng/mL. The samples were provided with a group containing polymyxin B, the macrophages could not produce TNF by the low molecular weight lipopolysaccharide. From this, it is obvious that the fermented rice powder extract has a biological activity different from those of the low molecular weight lipopolysaccharide and the limulus positive glycolipid.

TABLE 22

TNF production from macrophages by fermented rice powder extract and inhibitory effect of polymyxin B (TNF induction activity of fermented rice powder extract)

| Sample concentration (ng/ml) | Fermented rice powder extract with the addition of polymyxin B | Fermented rice powder extract without the addition of polymyxin B | Limulus positive glycolipid with the addition of polymyxin B | Limulus positive glycolipid without the addition of polymyxin B |
|---|---|---|---|---|
| 0 | 0 | 0 | 0 | 0 |
| 1 | 0 | 0 | 0 | 0.1 |
| 10 | 0 | 0 | 0 | 2.2 |
| 100 | 0 | 0.1 | 0 | 6.1 |
| 1000 | 0.1 | 0.6 | 0 | 23.9 |
| 10000 | 0.5 | 2.4 | 0 | 29.3 |

H. Examples Relating to Fermented Brown Seaweed Extract

Example 22

Production of Fermented Brown Seaweed Mekabu Extract (1) 1.0 L of water, 0.2 g of potassium (I) phosphate, 1.15 g of sodium II phosphate, 8 g of common salt and 0.2 g of potassium chloride were added to a 2 liter conical flask.

(2) A dried brown seaweed mekabu (20 g) was added to (1)

(3) (2) was sterilized by autoclave.

(4) Preparation of inoculum: One colony of *Pantoea agglomerans* isolated from the wheat flour was added to 5 ml of 2% brown seaweed mekabu medium previously prepared in the same composition, and fermented at 37° C. overnight (15 hours) by gently stirring to prepare the inoculum for the fermentation of the brown seaweed mekabu.

(5) The total amount of (4) was added to (3), and fermented at 37° C. for 72 hours by gently stirring.

(6) The fermented brown seaweed mekabu solution of (5) was extracted by heating at 120° C. for 20 minutes in the autoclave. This was centrifuged (Kubota 8800, 2,000 rpm, 10 minutes), and the supernatants were collected to make a fermented brown seaweed mekabu extract.

(7) Measurement of limulus active substance content by limulus assay: For measurement, a Toxi-color system supplied by Seikagaku Corporation was used, and Seikagaku Corporation Et-1 was used as a standard limulus active substance. The content of the limulus active substance in the fermented brown seaweed mekabu extract was measured to be 132 μg/mL.

Example 23

Immunopotentiation Action of Fermented Brown Seaweed Mekabu Extract

An acute myelogenic leukemia cell line, THP-1 ($1 \times 10^6$/250 μL, RPMI1640 medium containing 10% fetal calf serum) used as human macrophages were placed in a 48-well plate, and previously precultured for 30 minutes. Subsequently, 250 μL of the medium (final volume 500 μL) was added so that the final concentration of each sample was 1 to 10,000 ng/mL. The samples were provided with a group containing polymyxin B (12.5 μg/mL). After culturing for 4 hours, culture supernatants and the cells were collected. The TNF activity in the supernatants was measured by a cytotoxicity test using L-929. The results are shown in Table 23. The macrophages produced TNF even with the presence of polymyxin B by the fermented brown seaweed mekabu extract, but with the presence of polymyxin B, the macrophages could not produce TNF by the low molecular weight lipopolysaccharide. From this, it is obvious that the fermented brown seaweed mekabu extract has a biological activity different from those of the low molecular weight lipopolysaccharide and the limulus positive glycolipid.

TABLE 23

TNF production from macrophages by fermented brown seaweed mekabu extract and inhibitory effect of polymyxin B (TNF induction activity of fermented brown seaweed mekabu extract)

| Sample concentration (ng/ml) | Fermented brown seaweed mekabu extract with the addition of polymyxin B | Fermented brown seaweed mekabu extract without the addition of polymyxin B | Limulus positive glycolipid with the addition of polymyxin B | Limulus positive glycolipid without the addition of polymyxin B |
|---|---|---|---|---|
| 0 | 0 | 0 | 0 | 0 |
| 1 | 0 | 0 | 0 | 0.1 |
| 10 | 0 | 0 | 0 | 2.2 |
| 100 | 0 | 3.2 | 0 | 6.1 |
| 1000 | 2.4 | 14.4 | 0 | 13.9 |
| 10000 | 18.7 | 31.8 | 0 | 29.3 |

INDUSTRIAL APPLICABILITY

According to the present invention, it becomes possible to inexpensively produce the fermented plant extract which is the safe immunopotentiator. The fermented plant extract obtained in this way can be utilized in pharmaceuticals, pharmaceuticals for animals, quasi drugs, cosmetics, foods, functional foods, feedstuff, and bath agents for mammals including humans (specifically domestic animals, pet animals, etc.), birds (specifically farmed chicken, pet birds, etc.), amphibian animals, reptiles, fish (specifically aqua cultured fish, pet fish, etc.) and invertebrates.

The invention claimed is:

1. A fermented plant extract obtained by a method comprising steps of:
   isolating *Pantoea agglomerans* from wheat flour;
   preparing a wheat flour preparation containing supplemental minerals;
   adding the isolated *P. agglomerans* to the wheat flour preparation;
   fermenting and culturing the wheat flour preparation at about 37° C.; and
   centrifuging the flour preparation to obtain the extract.

2. Fermented plant extract powder obtained from the fermented plant extract according to claim 1.

3. A pharmaceutical containing the fermented plant extract according to claim 1.

4. A food containing the fermented plant extract according to claim 1.

5. A bath agent containing the fermented plant extract according to claim 1.

6. A composition containing the fermented plant extract according to claim 1.

7. A pharmaceutical containing the fermented plant extract powder according to claim 2.

8. A food containing the fermented plant extract powder according to claim 2.

9. A bath agent containing the fermented plant extract powder according to claim 2.

10. A composition containing the fermented plant extract powder according to claim 2.

11. A fermented plant extract obtained by a method comprising steps of:
    isolating *Pantoea agglomerans* from wheat flour;
    preparing a wheat flour preparation containing supplemental minerals;
    adding amylase to the wheat flour preparation;
    adding the isolated *P. agglomerans* to the wheat flour preparation;
    fermenting and culturing the wheat flour preparation; and
    centrifuging the flour preparation to obtain the extract.

\* \* \* \* \*